United States Patent [19]
Ritter et al.

[11] Patent Number: 6,031,015
[45] Date of Patent: *Feb. 29, 2000

[54] DENTAL MATERIALS BASED ON LIQUID CRYSTALLINE MONOMERS

[75] Inventors: Helmut Ritter, Wuppertal; Georg Draheim, Haan, both of Germany; Norbert Moszner, Eschen, Liechtenstein; Ulrich Salz, Lindau, Liechtenstein; Volker Rheinberger, Vaduz, Liechtenstein

[73] Assignee: Ivoclar AG, Liechtenstein

[ * ] Notice: This patent issued on a continued prosecution application filed under 37 CFR 1.53(d), and is subject to the twenty year patent term provisions of 35 U.S.C. 154(a)(2).

[21] Appl. No.: 08/682,327
[22] Filed: Jul. 17, 1996

[30] Foreign Application Priority Data

Jul. 18, 1995 [DE] Germany ............................ 195 25 941

[51] Int. Cl.[7] ............................ C08K 9/06; A61K 6/083; C08F 2/50; C08L 67/07
[52] U.S. Cl. .................................. 522/77; 522/81; 522/83; 522/96; 522/181; 522/182; 522/908; 522/179; 523/116; 523/117; 554/220; 554/221; 554/223; 433/228.1; 433/222.1; 106/35; 252/299.6; 252/299.64; 252/299.7; 252/229.01
[58] Field of Search ....................................... 522/181, 182, 522/96, 83, 908, 77, 81, 179; 523/116, 117; 554/220, 221, 223; 433/228.1, 222.1; 106/35; 252/299.6, 299.64, 299.7, 299.01

[56] References Cited

U.S. PATENT DOCUMENTS

| | | | |
|---|---|---|---|
| Re. 35,135 | 12/1995 | Sakashita et al. | 522/908 |
| 4,629,746 | 12/1986 | Michl et al. . | |
| 4,656,031 | 4/1987 | Lane et al. . | |
| 5,032,669 | 7/1991 | Kantor et al. | 528/176 |
| 5,063,255 | 11/1991 | Hasegawa et al. | 522/96 |
| 5,178,851 | 1/1993 | GaffAr et al. | 424/52 |

FOREIGN PATENT DOCUMENTS

| | | |
|---|---|---|
| 0367341 | 5/1990 | European Pat. Off. ............... 522/181 |
| 57042977 | 3/1982 | Japan . |
| 62063541 | 3/1987 | Japan . |

OTHER PUBLICATIONS

Ullmann's Encyclopedia of Industrial Chemistry, fifth edition, vol. A8, "Dental Materials", pp. 281–282 (1987).

Antonucci, et al., "New Initiator Systems for Dental Resins Based on Ascorbic Acid," *J. Dent. Res.*, 58(9):1887–1899 (1979).

Kawaguchi, et al., "Synthesis and Physical Properties of Polyfunctional Methacrylates (Part 4). Synthesis and Physical Properties of Aromatic Dimethacrylate Copolymers," *Dental Materials Journal*, 3(2):272–279 (1984).

*Primary Examiner*—Susan W. Berman
*Attorney, Agent, or Firm*—Nixon Peabody LLP

[57] ABSTRACT

A dental material based on polymerizable monomers is described which contains at least one polymerizable monomer which has liquid crystalline properties. Compared with traditional materials, the dental material displays a lower decrease in volume upon polymerization and, because of its low viscosity, higher filler contents can be achieved.

14 Claims, 4 Drawing Sheets

TERMINAL ARRANGEMENT OF THE METHACRYLIC OR ACRYLIC GROUPS

LATERAL ARRANGEMENT OF THE METHACRYLIC OR ACRYLIC GROUPS

MIXED ARRANGEMENT OF THE METHACRYLIC OR ACRYLIC GROUPS

TERMINAL ARRANGEMENT OF THE METHACRYLIC OR ACRYLIC GROUPS
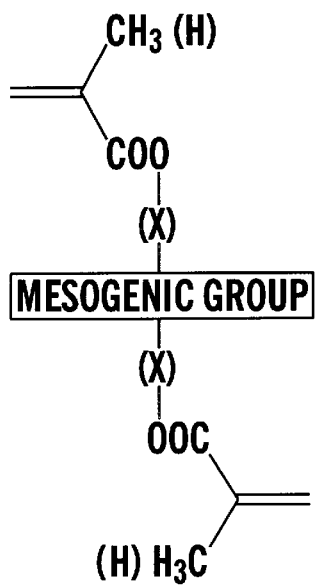
LATERAL ARRANGEMENT OF THE METHACRYLIC OR ACRYLIC GROUPS
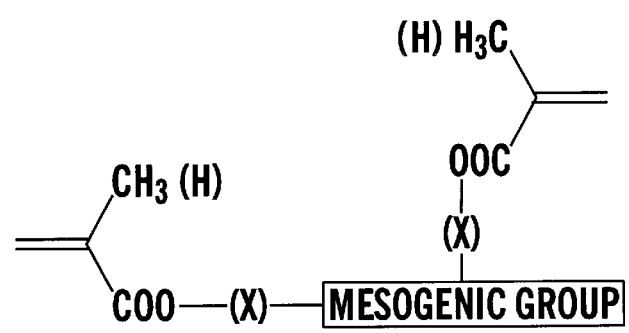
MIXED ARRANGEMENT OF THE METHACRYLIC OR ACRYLIC GROUPS
*FIG. 2*

DENTAL MATERIALS BASED ON LIQUID CRYSTALLINE MONOMERS

The present invention relates to dental materials based on polymerizable monomers which have liquid crystalline properties.

BACKGROUND OF THE INVENTION

Traditional polymerizable dental materials, as are for example described in EP-0 091 990 A2, in most cases contain crosslinked bi- or polyfunctional acrylates and methacrylates which are predominantly radically polymerized. It is a disadvantage that in the case of all the polymerizable dental materials known to date, polymerization is associated with a clear decrease in volume. The shrinkage of customary monomer mixtures is in the range from 5 to 12% by vol. In the case of filled composite materials, the decrease in volume is in the range from 2.6 to 7.1% by vol. (A. J. Feilzer, A. J. DeGee, C. L. Davidson, J. Prosthet. Dent. 59 (1988) 297).

The reduction in volume means that no adequate, load-resistant marginal adaption can be achieved, particularly in the side tooth region (I. Kerjci, Zahnfarbene Restaurationen, Hanser Verlag Munich/Vienna, 1992, page 5 et seq.). In the case of poor marginal edge adaption, there is the danger, particularly in regions which are only poorly accessible by dental hygiene measures, that bacteria will find their way between tooth and filling and thus damage the pulp or trigger the formation of secondary caries. Moreover, a reduction in volume upon polymerization has a negative effect on the mechanical properties of the material.

Although dental material shrinkage upon polymerization can be reduced by using monomers with higher molecular weights whilst simultaneously lowering the percentage proportion of the polymerizable group relative to the molecular weight of the molecule, the molecular weight increase brings about a considerable, undesired increase in the viscosity of the dental material, which makes its further processing, such as for example the incorporation of fillings, considerably more difficult.

The polymerization of liquid crystalline (LC) monomers produces so-called side-chain liquid crystalline polymers (SCLCP). These are suitable primarily for reversible information storage, the production of media with non-linear optical properties, for the production of optoelectronic construction elements, as separating phases for chromatographic procedures and as coating materials (J. Rübner, R. Ruhmann, G. Rodekirch, Plaste und Kautschuk 36 (1989) 253).

In most cases, polymerizable liquid crystalline monomers contain styrene or (meth)acrylate groups as polymerizable groups, whilst their mesogenic groups are frequently derived from aromatic carboxylic acid esters, azomethines or steroids (A. Blumenstein, Liquid Cristalline Order in Polymers, Academic Press, New York, 1978, page 105; J. H. Wendorff, Flüssigkristalline Polymere, C. Hanser Verlag, Munich/Vienna, 1989). Liquid crystalline monomers can for example be polymerized by light (D. J. Broer, K. Katsumi, Makromol. Chem. 189 (1988) 185), ionically, such as for example in the case of the cationic polymerization of liquid crystalline vinyl ethers (H. Jonson, H. Andersson, P. E. Sundell, U. W. Gudde, A. Hult, Polym. Bull. 25 (1991) 641) and by group transfer polymerization, such as for example in the case of liquid crystalline methacrylates (W. Kreuder, O. W. Webster, H. Ringsdorf, Makromol. Chem., Rapid Commun. 7 (1986) 5).

In addition to liquid crystalline compounds with a polymerizable group in the molecule, various difunctional liquid crystalline monomers are known, for example diacrylates (S. C. Lin, E. M. Pearce, High-Performance Thermosets, Hanser Pub. Munich, Vienna, New York, 1993, page 270), divinyl ethers (H. Andersson, F. Sahlen, U. W. Gedde, A. Hult, Macromol. Symp. 77 (1994) 339) or diepoxides (S. Jahromi, J. Lub, G. N. Mol, Polymer 35 (1994) 622). The polymerization of difunctional liquid crystalline monomers produces ordered network polymers.

The use of liquid crystalline monomers for the production of dental materials has not been described to date.

BRIEF SUMMARY OF THE INVENTION

It is the object of the invention to provide a dental material which shows only a slight decrease in volume upon polymerization, has a low viscosity before polymerization and a good mechanical strength after hardening.

This object is achieved by dental materials based on polymerizable monomers which contain at least one monomer which has liquid crystalline properties.

Those substances which have a state of molecular order between that of the liquid and that of the crystal are called liquid crystalline. In the liquid crystalline state, these substances display the mobility of liquids and anisotropic properties typical of crystals. The anisotropic properties are not lost until the transition from the anisotropic-liquid to the isotropic-liquid state (clarifying point). The liquid crystalline state is also called the mesophase and substances or groupings which form a mesophase in a certain temperature range are called mesogenic or mesogenic groups.

Surprisingly, upon polymerization, the dental materials according to the invention show a decrease in volume of only ca. 3.5% by vol., which represents a clear improvement vis-à-vis known polymerizable dental materials. In the case of the preferred materials, the shrinkage is less than 3.0% by vol. Moreover, they have a clearly lower viscosity than comparable traditional dental materials, which permits the incorporation of greater quantities of filler and thus a further reduction in shrinkage during polymerization.

Particularly good results are achieved with monomers which have liquid crystalline properties in the range between 10 and 150° C., in particular in the range from 30 to 75° C.

The monomers according to the invention preferably contain 1 to 6, particularly preferably 1 to 4 and quite especially preferably 1 or 2 polymerizable groups. Monomers which contain as polymerizable groups one or more ethylenically unsaturated group(s), one or more epoxide, vinyl ether, 1,3-dioxolane, 1,3-dioxepane, spiro-orthoester and/or spiro-orthocarbonate group(s) are preferred. Monomers which contain a vinyl group, quite particularly preferably those which contain an acryl- or methacrylate group, are particularly preferred.

Also, the monomers according to the invention preferably contain 1, 2 or 3 mesogenic groups.

Particularly suitable are monomers which have as mesogenic group an aromatic carboxylic acid ester and/or steroid group, in particular a 2,5-alkoxy terephthalate group. The 2,5-alkoxy terephthalate group contains preferably branched or unbranched alkoxy groups with 1 to 30 carbon atoms. Particularly preferred are alkoxy groups with 3 to 18, in particular with 6 to 12 carbon atoms. Straight-chained alkoxy groups are also preferred to branched groups.

The polymerizable group or groups can be arranged terminally and/or laterally relative to the mesogenic group.

The polymerizable group can be bonded to the mesogenic group directly or via a spacer. Suitable spacers are alkylene and oxyalkylene chains with 1 to 18 carbon or carbon and oxygen atoms. Spacers according to formula $-[O(-CH_2)_j]_k-$, where i (j)=0 to 18, preferably 2 to 12, and k(l)=0 to 10, preferably 0 to 4, are preferred.

BRIEF DESCRIPTION OF THE DRAWINGS

The terminal or lateral arrangement of a polymerizable methacrylate or acrylate group for monomers with one mesogenic group is shown in FIG. 1.

FIG. 2 shows the terminal, the lateral and the mixed arrangement of polymerizable methacrylate or acrylate groups for liquid crystalline monomers with two polymerizable groups and one mesogenic group.

Figure 1:
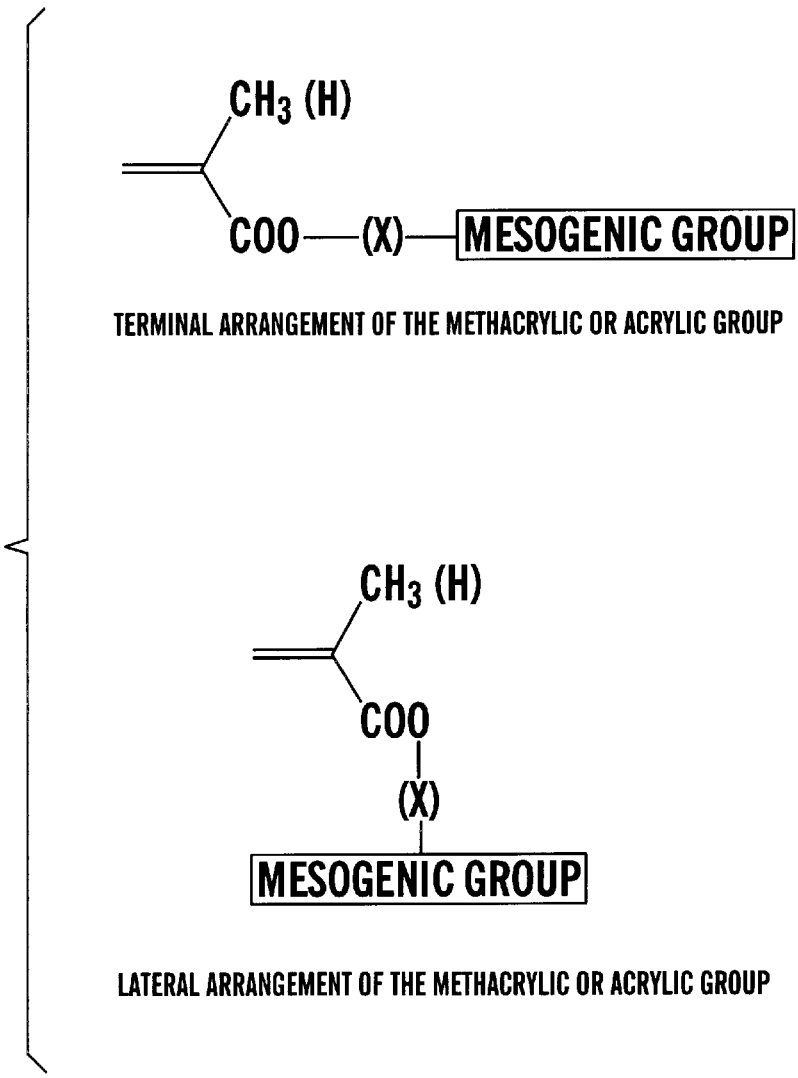

Preferred monomers with terminal polymerizable groups are terephthalic acid derivative is esterified according to the oxalyl chloride method with an excess of hydroquinone to give the corresponding diol. The final reaction with methacrylic acid chloride produces the liquid crystalline dimethacrylate with methacrylate function in end-position relative to the mesogenic group. This synthesis sequence is shown by way of example in FIG. 3.

Preferred liquid crystalline monomers with polymerizable groups arranged laterally relative to the mesogenic group are monomers based on cholesterol derivatives, particularly

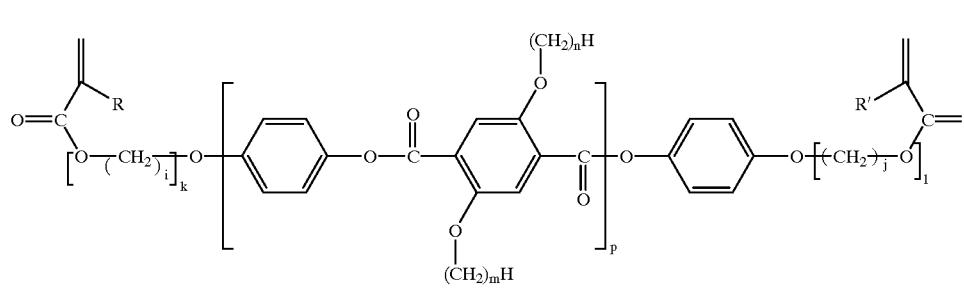

Formula I wherein R, R'=H or $CH_3$; i, j=0 to 18, preferably 2 to 12; k, l=0 to 10, preferably 0 to 4; m, n=1 to 30, preferably 3 to 18

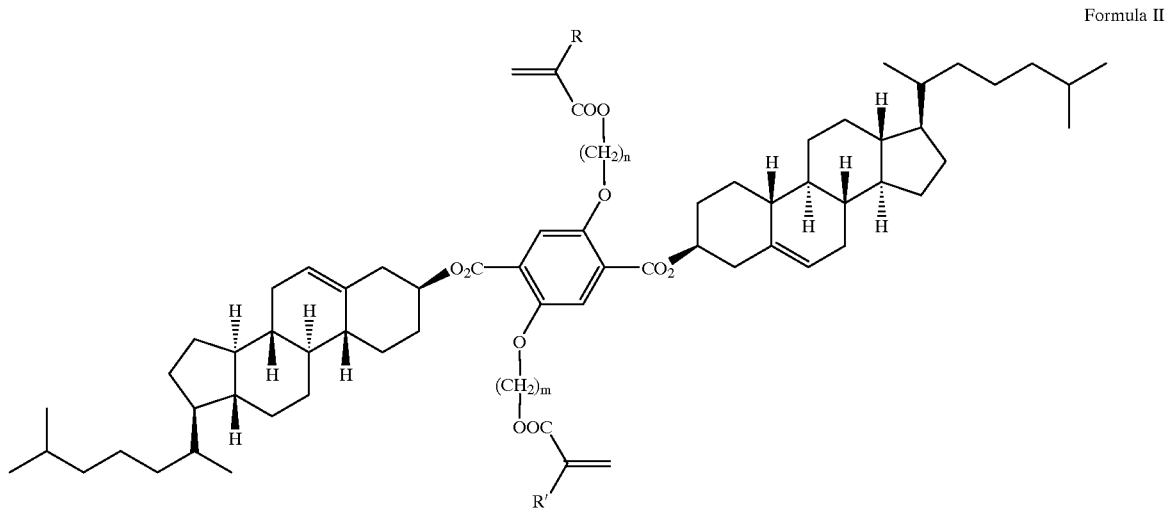

Formula II and particularly preferably 6 to 12 and p=0 to 10, preferably 1 to 5. R and R', i and j, k and l, and m and n can in each case be the same or different.

These derivatives can be produced in known manner, for example starting from diethyl-2,5-dihydroxyterephthalate. The starting compound is firstly reacted with a suitable alkyl bromide according to a Williamson ether synthesis to give the corresponding alkoxy derivative. After subsequent saponification of the terephthalic acid diester, the obtained where R, R' are in each case H or $CH_3$ and n, m are the same or, independently of one another, 1 to 30, preferably 3 to 18 and particularly preferably 2 to 12.

These derivatives can be produced by known reactions, for example starting from diethyl-2,5-dihydroxyterephthalate. The starting compound is firstly reacted with a suitable dibromoalkane according to a Williamson ether synthesis. The alkoxy side groups are then acetylated, complete saponification of the ester groups then leads to the dicarboxylic acid diol, which produces the corresponding dimethacrylate after reaction with methacrylic acid chloride. The dimethacrylate is then reacted with cholesterol according to the oxalyl chloride method to give the desired liquid crystalline monomer. This synthesis sequence is shown by way of example in FIG. 4.

DETAILED DESCRIPTION OF THE INVENTION

The dental materials are produced by mixing the monomers according to the invention with one or more polymerization initiators and optionally other non-liquid crystalline monomers and fillers.

Unfilled dental materials essentially contain one or more liquid crystalline monomers and an initiator. They are particularly suitable as adhesives or for preventive dentistry, for example as a constituent of enamelling systems, releasing fluoride or antimicrobial active ingredients, for the prevention of caries.

Suitable as non-liquid crystalline monomers for combining with the monomers according to the invention are in particular triethylene glycol dimethacrylate, tetraethylene glycol dimethacrylate, butanediol dimethacrylate, hexanediol dimethacrylate, decanediol dimethacrylate and/or dodecanediol dimethacrylate. The quantity of non-liquid crystalline monomers is selected such that the formation of mesophases is not prevented. Dental materials which were obtained exclusively using liquid crystalline monomers are preferred.

Filled dental materials also contain one or more fillers. Preferred fillers are disclosed in U.S. Pat. No. 4,629,746 and U.S. patent application Ser. No. 08/025,810. They preferably have an average particle size in the range from 0.01 to 5 μm. Filled dental materials are particularly suitable as filling material, inlay, veneer or onlay material, dental cement, facing material for crowns and bridges, material for artificial teeth or other materials for prosthetic and preservation dentistry. The filler content is preferably in the range from 1 to 85% by wt.

The dental materials according to the invention can be polymerized radically, ionically or using a combination of radical and ionic initiators, radical polymerization being preferred. Depending on the type of initiator used, the dental material can be polymerized hot, cold or using light. The known peroxides such as dibenzoyl peroxide, dilauroyl peroxide, tert.-butyl peroctoate or tert.-butyl perbenzoate can be used as initiators for the hot polymerization. Furthermore, 2,2'-azoisobutyric acid nitrile (AIBN), benzpinacol and 2,2'-dialkyl benzpinacols are also suitable.

Benzophenone and its derivatives and benzoin and its derivatives for example can be used as initiators for the photopolymerization. Other preferred photoinitiators are the α-diketones such as 9,10-phenanthrenequinone, diacetyl, furil, anisil, 4,4'-dichlorobenzil and 4,4'-dialkoxybenzil. Camphor quinone is used particularly preferably. Furthermore, the group of the acyl phosphinoxides is also well suited for initiating the photopolymerization of liquid crystalline acrylate and methacrylate monomers. To accelerate the initiation, the photoinitiators are preferably used together with a reducing agent, particularly preferably with an amine, especially an aromatic amine.

Used as initiators for the cold polymerization are radical-supplying redox systems, for example benzoyl or lauroyl peroxide together with amines such as N,N-dimethyl-p-toluidine, N,N-dihydroxyethyl-p-toluidine or other structurally related amines.

The combination of photoinitiators with various redox systems has proved successful particularly in the case of dental materials for the cementing of dental restorations, such as for example glass ceramic inlays, onlays, partial crowns and crowns.

Combinations of camphor quinone, benzoyl peroxide and amines such as for example N,N-dimethyl-p-toluidine and/or N,N-cyanoethyl ethylaniline are preferred.

The concentration of the initiators is preferably in the range from 0.05 to 1.5% by wt., particularly preferably in the range from 0.2 to 0.8% by wt., relative to the weight of the monomer used.

The invention is described in more detail below with reference to embodiments.

EXAMPLES

Figure 3:
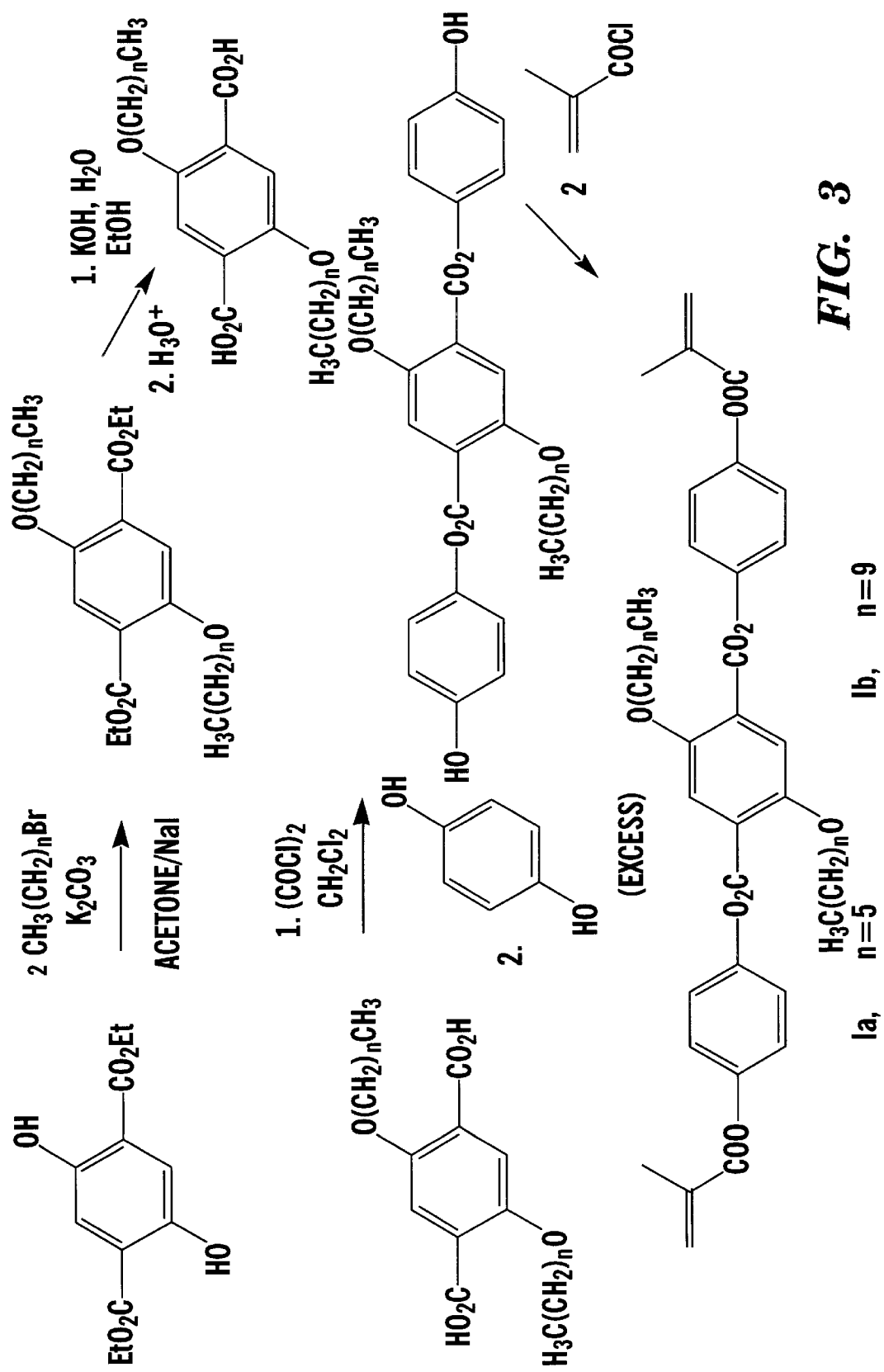

I. Synthesis of 2,5-di(hexoxy)terephthalic acid-di-(4-methacryloylhydroquinone)ester (FIG. 3, Ia)

Example 1

Synthesis of 2,5-dihexoxyterephthalic acid diethyl ester 15.0 g (59.0 mmol) diethyl-2,5-dihydroxyterephthalate, 20.0 ml (142 mmol) 1-bromohexane, 28.0 g (203 mmol) $K_2CO_3$ and 200 mg NaI in 100 ml acetone are heated under reflux for 66 hours. The initially yellow suspension becomes largely decolorized. The solvent is then distilled off and the residue is taken up in 400 ml ethyl acetate and 200 ml water. After removing the aqueous phase, the organic phase is washed three times with 80 ml 1 N NaOH and three times with 100 ml water and then dried over $Na_2SO_4$. After distilling off the ethyl acetate, the residue is taken up in petroleum ether. At −30° C., colourless crystals form which are recrystallized again from petroleum ether.

Yield: 16.9 g (68%) colourless crystals

Melting point: 41° C.

$C_{24}H_{38}O_6$ (422.56) Calc. C 68.22 H 9.06 Found C 68.27 H 9.01

Example 2

Synthesis of 2,5-dihexoxyterephthalic acid

A mixture of 8.91 g (135 mmol) 85% aqueous KOH solution and 20 ml water is added to 16.3 g (38.57 mmol) 2,5-dihexoxyterephthalic acid diethyl ester in 20 ml ethanol and the whole is stirred for 2 hours at 90° C. The crude product precipitated by the dropwise addition of 12.5 ml conc. HCl with ice-cooling is filtered off, washed neutral with water and recrystallized from ethanol.

Yield: 12.02 g (85%) colourless crystals

Melting point: 140 to 141° C.

Example 3

Synthesis of 2,5-dihexoxyterephthalic acid dihydroquinone ester (2,5-dihexoxyterephthalic acid di-4-hydroxyphenyl ester)

5.63 ml (65.5 mmol) oxalyl chloride are added to a suspension of 2.0 g (5.46 mmol) 2,5-dihexoxyterephthalic acid in 15.0 ml abs. methylene chloride and the whole is stirred at 25° C. for 24 h. After removing the solvent and excess oxalyl chloride in a vacuum, the residual solid dichloride is taken up in 10.0 ml absol. THF. With ice-cooling and stirring, a solution of 18.02 g (163.8 mmol) hydroquinone in 40 ml absol. THF is then added dropwise to the yellow solution, followed by 11.5 ml (82.1 mmol) triethylamine. The mixture is then stirred for 5 h at 0° C. The reaction mixture is acidified by the dropwise addition of 80 ml 1N HCl with ice-cooling, and the THF is then largely distilled off under vacuum. After adding 250 ml water, the precipitating crude product is filtered off, washed three times with water (3×50 ml), and recrystallized twice from methanol.

Yield: 2.20 g (73%)

$C_{32}H_{38}O_8$ (550.65) Calc. C 69.80 H 6.96 Found C 70.00 H 7.06

Example 4

Synthesis of 2,5-dihexoxyterephthalic acid di-(4-methacryloylhydroquinone)ester (2,5-dihexoxyterephthalicacid-di-4-oxymethacryloylphenylester)

Firstly 0.53 ml (5.46 mmol) methacryloyl chloride, then 0.82 ml (5.86 mmol) absol. triethylamine are added dropwise, with ice-cooling, to a suspension of 1.0 g (1.82 mmol) 2,5-dihexoxyterephthalic acid-di-4-hydroxyphenyl ester in 10.0 ml absol. methylene chloride and the whole is stirred at room temperature for 4 h. After removing the solvent in a vacuum, the residual residue is taken up in 20 ml ethyl acetate and the ammonium salt is filtered off. The filtrate is stirred vigorously with a solution of 2.0 g (18.7 mmol) $Na_2CO_3$ in 30 ml water for 2 h, then the organic phase is removed, washed twice with 50 ml 1N HCl and 30 ml water and dried over $Na_2SO_4$. After distilling off the solvent in a vacuum, the crude product is recrystallized once from methanol and once from petroleum ether.

Yield: 810 mg (65%) colourless crystals

Melting point: 75 to 78° C. (phase transition from the crystalline phase to the liquid crystalline phase); 78 to 96° C. (cloudy melt); above 96° C. (clear melt; phase transition from the liquid crystalline phase to the isotropic melt);

$C_{40}H_{46}O_{10}$ (686.80) Calc. C 69.95 H 6.75 Found C 69.89 H 6.85

$^1$H-NMR (CDCl$_3$, 400 MHz); δ=0.92 (t, 6H, CH$_2$CH$_2$CH$_3$); 1.32–1.41 (m, 8H, CH$_2$); 1.51–1.58 (m, 4H, OCH$_2$CH$_2$CH$_2$); 1.85–1.92 (m, 4H, OCH$_2$CH$_2$); 2.12 (ps, 6H CH$_3$); 4.14 (t, 4H, OCH$_2$); 5.81 (ps, 2H, alkene); 6.40 (ps, 2H, alkene); 7.25; 7.32 (pd, 4H, ArCO$_2$CCH, aromatic substance; pd, 4H, CH$_2$=C(CH$_3$)CO$_2$CCH, aromatic substance); 7.61 (s, 2H, aromatic substance).

MS (70 eV): m/z=686 [M$^+$], 509, 510 [M$^+$ —CH$_2$=C(CH$_3$)CO$_2$(C$_6$H$_4$)O]

Figure 4:
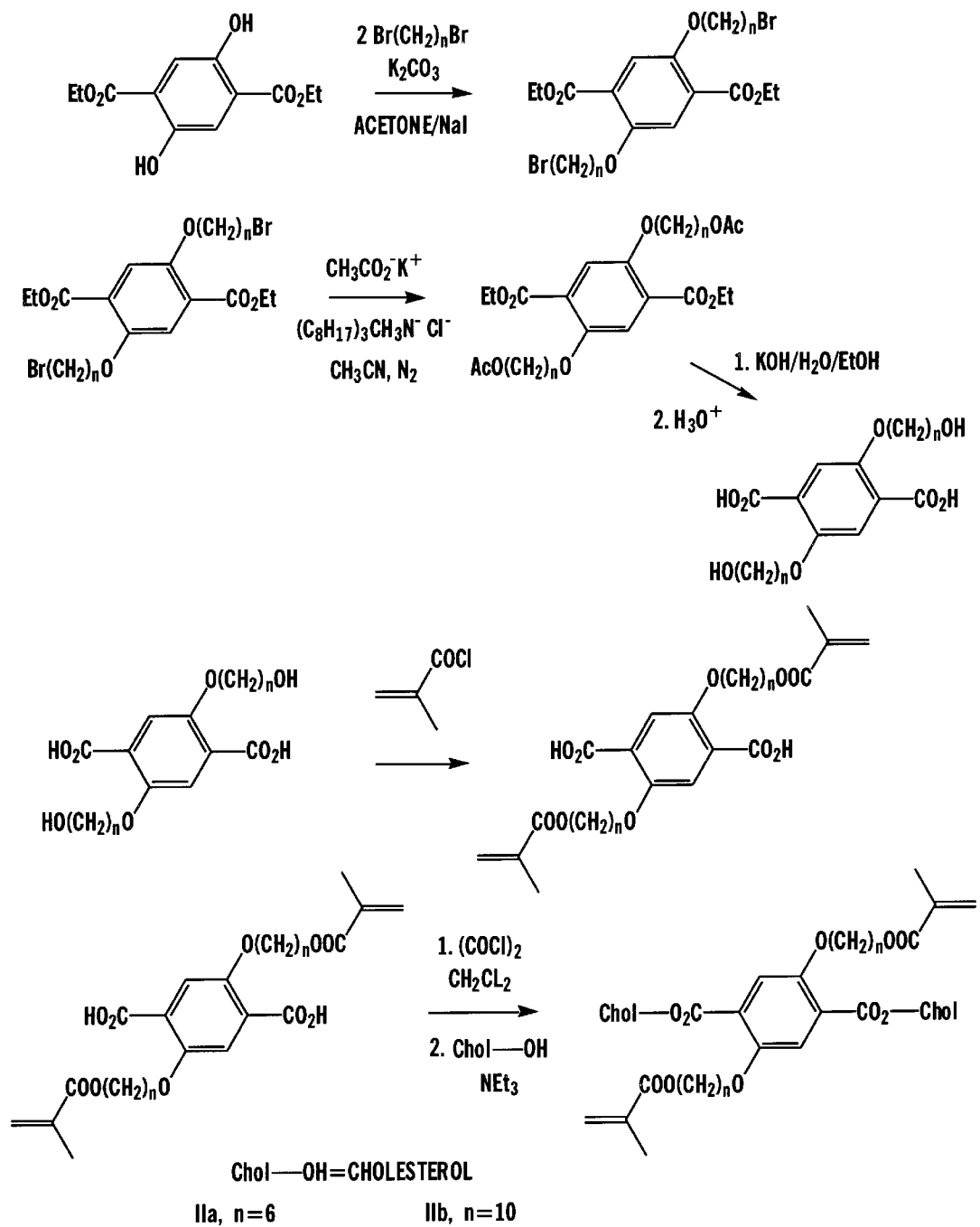

II. Synthesis of 2,5-bis-[6-(oxymethacryloyl)hexoxy]terephthalic acid dicholesteryl ester (FIG. 4, IIa)

Example 5

Synthesis of diethyl-2,5-bis-(6-bromohexoxy)terephthalate 25.4 g (0.1 mol) diethyl-2,5-dihydroxyterephthalate, 232 ml (1.5 mol) 1,6-dibromohexane, 130 g (0.94 mol) K$_2$CO$_3$ and 200 mg NaI in 200 ml acetone are heated under reflux for 12 hours. The initially yellow suspension decolorizes. After distilling off the solvent, 1200 ml diethyl ether are added to the reaction mixture and the whole is washed twice, each time with 200 ml water. The organic phase is then dried over $Na_2SO_4$ and the solvent is distilled off. The colourless product which crystallized out after adding 250 ml petroleum ether at –20° C. is recrystallized once from petroleum ether and twice from ethanol.

Yield: 52.6 g (91%) colourless crystals

Melting point: 58 to 60° C.

$C_{24}H_{36}Br_2O_6$ (580.35): Calc. C 49.67 H 6.25 Found C 49.94 H 6.28

Example 6

Synthesis of diethyl-2,5-bis-(6-acetoxyhexoxy)terephthalate 50.0 g (86.0 mmol) diethyl-2,5-bis-(6-bromohexoxy)terephthalate, 84.5 g (861 mmol) potassium acetate and 4.4 g (11 mmol) methyl trioctyl ammonium chloride (Aliquat 336®, tricaprylyl methyl ammonium chloride, Fluka, CAS 5137.55.3) in 500 ml absolute acetonitrile are heated under reflux in a nitrogen atmosphere for 48 hours. After distilling off the solvent, the reaction mixture is taken up in 1200 ml ethyl acetate and washed three times with water (3×300 ml). The organic phase is dried over MgSO$_4$ and the solvent is then distilled off. 1000 ml petroleum ether is added to the residual, oily residue and the product crystallizing out after 16 hours at –20° C. is recrystallized from petroleum ether/ethyl acetate.

Yield: 40.3 g (87%) colourless crystals

Melting point: 46 to 47° C.

$C_{28}H_{42}O_{10}$ (538.63) Calc. C 62.44 H 7.86 Found C 62.49 H 7.85

Example 7

Synthesis of 2,5-bis-(6-hydroxyhexoxy)terephthalic acid

A solution of 25.0 g (379 mmol) 85% KOH in 300 ml water is added to 40.0 g (74.3 mmol) diethyl-2,5-bis-(6-acetoxyhexoxy)terephthalate in 250 ml ethanol and the whole is heated under reflux for 1.5 hours. After distilling off approx. 150 ml ethanol, the reaction mixture is acidified by adding 40.0 g conc. HCl and stored at 2° C. for 20 hours for complete crystallization of the crude product. The colourless crude product is then filtered off, washed neutral with water and recrystallized from ethanol.

Yield: 27.8 g (94%) colourless crystals

Melting point: 137 to 139° C.

$C_{28}H_{30}O_8$ (398.45): Calc. C 60.29 H 7.59 Found C 60.45 H 7.46

Example 8

Synthesis of 2,5-bis-[6-(oxymethacryloyl)-hexoxy]terephthalic acid 38.9 ml (405 mmol) methacryloyl chloride and 56.7 ml (405 mmol) triethylamine are added, with stirring, to a mixture of 27.0 g (67.8 mmol) 2,5-bis-(6-hydroxyhexoxy)-terephthalic acid and 20 mg hydroquinone monopropyl ether in 400 ml absolute THF and the whole is then stirred for a further 24 hours. After distilling off approx. 250 ml solvent, 28.6 g (270 mmol) $Na_2CO_3$ in 150 ml water are added and stirring is continued for 48 hours at room temperature. The suspension is acidified by adding 50 ml conc. HCl and 200 ml water. The organic phase is removed and washed three times with water and then dried over $Na_2SO_4$. After adding 50 mg hydroquinone monopropylether and 10 g activated charcoal, the mixture is stirred for 30 minutes under slight reflux. The activated charcoal is then filtered off and the solvent is removed by distillation. 300 ml diethyl ether are added to the residue. After 24 hours at −26° C., yellow crystals form which are recrystallized again from diethyl ether/ethyl acetate.

Yield: 18.8 g (52%) yellowish crystals

Melting point: 102.5° C.

$C_{28}H_{38}O_{10}$ (534.60): Calc. C 62.91 H 7.16 Found C 62.79 H 7.35

Example 9

Synthesis of 2,5-bis-[6-(oxymethacryloyl)hexoxy] terephthalic acid dicholesteryl ester 15.0 ml (175 mmol) oxalyl chloride are added under reflux to 5.00 g (9.35 mmol) 2,5-bis-[6-(oxymethacryloyl) hexoxy]terephthalic acid and 10 mg hydroquinone monopropyl ether in 30 ml absolute methylene chloride. The mixture is stirred for a further 72 hours and the solvent is distilled off in vacuum at 50° C. To the oily residue is added dropwise, with stirring, a solution of 7.23 g (18.7 mmol) cholesterol in 10 ml absolute THF and then, with ice-cooling, 3.0 ml triethylamine. After adding 10 mg hydroquinone monopropylether, the mixture is then stirred for 6 days at room temperature, then the solvent is distilled off and the residue taken up in 200 ml diethyl ether. The organic phase is washed three times with water (3×50 ml), and then dried over $Na_2SO_4$. After distilling off the solvent, a brownish, oily crude product is obtained which is recrystallized firstly from ethyl acetate/isopropanol and then from THF/ethanol.

Yield: 10.9 g (92%) colourless crystals

Melting point: 75 to 80° C.

IR (KBr): 3010 - 2820 (C—H), 1715 (C=O; terephthalate), 1705 (C=O; methacrylate), 1635 (C=C; alkene), 1495 cm$^{-1}$ (C=C; aromatic substance).

$^1$H-NMR (CDCl$_3$, 400 MHz): δ=0.69–2.04 (82H, aliph. H, cholesterol structure; 16H, $CH_2$, spacer), 1.94 (ps, 6H, $CH_2$=C—$CH_3$), 2.46 (m, 4H, $CO_2CHCH_2$—C=CH—, cholesterol structure), 4.00 (t, 4H, ArO$CH_2$—), 4.15 (t, 4H, $CO_2CH_2$—), 4.86 (m, 2H, Ar$CO_2$CH), 5.42 (m, 2H, alkene, cholesterol structure), 5.53 (ps, 2H, $CH_2$=C—$CH_3$), 6.09 (ps, 2H, $CH_2$=C—$CH_3$), 7.30 (s, 2H, aromatic substance).

$C_{82}H_{126}O_{10}$ (1271.89): Calc. C 77.44 H 9.99 Found C 77.32 H 10.01

III. Synthesis of 2,5-bis-[10-(oxymethacryloyl) decoxy]terephthalic acid dicholesteryl ester (FIG. 4, IIb)

Example 10

Synthesis of diethyl-2,5-bis-(10-bromedecoxy) terephthalate 25.4 g (0.1 mol) diethyl-2,5-dihydroxyterephthalate, 450 g (1.5 mol) 1,10-dibromodecane, 138 g (1.0 mol) $K_2CO_3$ and 200 mg NaI in 200 ml acetone are heated under reflux for 28 hours until the originally yellow suspension has decolorized. After distilling off the solvent, the reaction mixture is extracted twice with diethyl ether (2×250 ml), and insoluble salts are filtered off. The filtrate is washed twice with 200 ml water and dried over $Na_2SO_4$. The solvent is then distilled off. The colourless, solid residue is washed twice with petroleum ether and then recrystallized from petroleum ether.

Yield: 51.7 g (75%)

$C_{32}H_{52}Br_2O_6$ (692.56) Calc. C 55.50 H 7.57 Found C 55.78 H 7.58

Example 11

Synthesis of diethyl-2,5-bis-(10-acetoxydecoxy) terephthalate 46.4 g (67.0 mmol) diethyl-2,5-bis-(10-bromodecoxy) terephthalate, 65.8 g (671 mmol) potassium acetate and 3.4 g (8.5 mmol) Aliquat 336® in 350 ml absolute acetonitrile are heated under $N_2$ under reflux for 48 hours. After distilling off the solvent, the reaction mixture is taken up in 300 ml chloroform, insoluble salts are filtered off and the filtrate is washed twice with 150 ml water. The organic phase is dried over $Na_2SO_4$ and the solvent is then distilled off. 300 ml petroleum ether are added to the remaining, oily residue, the product crystallising out after 16 hours at −20° C. It is then recrystallized from ethanol.

Yield: 38.5 g (88%)

$C_{36}H_{58}O_{10}$ (650.85) Calc. C 66.44 H 8.98 Found C 66.45 H 9.20

Example 12

Synthesis of 2,5-bis-(10-hydroxydecoxy) terephthalic acid

A solution of 20.0 g (303 mmol) 85% aqueous KOH in 200 ml water is added to 38.0 g (58.4 mmol) diethyl-2,5-bis-(10-acetoxydecoxy)terephthalate in 200 ml ethanol and the whole is heated under reflux for 1.5 hours. 28.0 ml conc. HCl are then added dropwise with ice-cooling and stirring until the solution shows an acidic pH. The precipitated, colourless crude product is filtered off, washed neutral and recrystallized from ethanol and methanol/acetone.

Yield: 25.0 g (84%)

$C_{28}H_{46}O_8$ (510.66) Calc. C 65.86 H 9.08 Found C 65.62 H 9.30

Example 13

Synthesis of 2,5-bis-[10-(oxymethacroyl)decoxy] terephthalic acid 30.0 ml (311 mmol) methacroyl chloride and 43.8 ml (313 mmol) triethylamine are added, with stirring at 0° C., to a mixture of 15.0 g (29.4 mmol) 2,5-bis-(10-hydroxydecoxy) terephthalic acid and 20 mg hydroquinone monopropyl ether in 150 ml abs. THF, and the whole is then stirred for a further 48 hours at 40° C. After distilling off approx. 75 ml of the solvent, 25.0 g (236 mmol) $Na_2CO_3$ in 200 ml water are added to the reaction mixture and the mixture is stirred for 48 hours at room temperature. The suspension is acidified by adding 120 ml semi-conc. HCl and 200 ml water at 0° C. After removing the aqueous phase, the residual oily crude product is taken up in 100 ml methanol and water is added dropwise with stirring. The precipitated product is filtered off and then recrystallized, once from ethanol and once from ethyl acetate.

Yield: 11.38 g (60%)

Melting point: 72 to 74° C., up to 116° C. the melt remains cloudy, above this, a clear melt exists.

$C_{36}H_{54}O_{10}$ (646.82): Calc. C 66.85 H 8.42 Found C 66.71 H 8.51

Example 14

Synthesis of 2,5-bis-[10-(oxymethacryloyl)decoxy] terephthalic acid dicholesteryl ester 6.66 ml (77.3 mmol) oxalyl chloride are added dropwise, at 0° C. with stirring, to a solution of 5.00 g (7.73 mmol) 2,5-bis-[10-(oxymethacroyl)-decoxy]terephthalic acid in 20 ml abs. methylene chloride. The mixture is stirred for a further 24 hours and then the solvent and excess oxalyl chloride are distilled off in a high vacuum at room temperature. The residue is taken up with 15 ml abs. THF and a solution of 15.0 g (38.75 mmol) cholesterol in 20 ml abs. THF and then 7.0 ml triethylamine are added dropwise with stirring. After adding 10 mg hydroquinone monopropyl ether, the mixture is stirred for 120 hours at 45° C., the solvent is distilled off, the yellow residue is extracted with a total of 400 ml diethyl ether and undissolved ammonium salt is filtered off. The filtrate is concentrated in a vacuum to a volume of approx. 50 ml and 300 ml methanol are added with stirring. The obtained oily crude product is washed several times with methanol and then purified by means of column chromatography. An oily product is obtained which clearly becomes more thinly liquid at a temperature of 70° C. or more.

Yield: 6.95 g (65%)

IR (KBr): 2950 - 2830 (C—H), 1715 (C=O; terephthalate), 1695 (C=O; methacrylate), 1635 (C=C; alkene), 1500 cm$^{-1}$ (C=C; aromatic substance).

$^1$H-NMR (CDCl$_3$, 400 MHz): δ=0.73–2.08 (82H, aliph. H, cholesterol structure; 32H, CH$_2$, spacer); 1.98 (ps. 6H, CH$_2$=C—CH$_3$); 2.50 (m, 4H, CO$_2$CHCH$_2$—C=CH—, cholesterol structure); 4.02 (t, 4H, ArOCH$_2$—); 4.17 (t, 4H, CO$_2$CH$_2$—); 4.90 (m, 2H, ArCO$_2$CH); 5.45 (m, 2H, alkene, cholesterol structure); 5.57 (ps, 2H, CH$_2$=C—CH$_3$); 6.13 (ps, 2H, CH$_2$=C—CH$_3$); 7.33 (s, 2H, aromatic substance).

C$_{82}$H$_{126}$O$_{10}$ (1384.11) Calc. C 78.10 H 10.34 Found C 78.09 H 10.41

Example 15

Determination of the polymerization shrinkage of 2,5-bis-[10-(oxymethacryloyl)decoxy]terephthalic acid dicholesteryl ester (FIG. 4, IIb)

0.3% camphor quinone and 0.5% N-2-cyanoethyl-N-methylaniline at 50° C. are added to 2,5-bis-[10-oxymethacryloyl)decoxy]terephthalic acid dicholesteryl ester and the whole is homogeneously mixed. After cooling to room temperature, the mixture was polymerized 2×3 minutes in a Spectramat (dental light polymerization device from Ivoclar). Subsequent determination of the polymerization shrinkage gave a value of only 1.32% by vol. Parallel to this, a sample of bis-GMA was polymerized as described above. The polymerization shrinkage was 6.0% by vol.

Example 16

Production of a dental material based on 2,5-bis-[10-(oxymethacryloyl)decoxy]terephthalic acid dicholesteryl ester (FIG. 4, IIb)

A composite securing cement based on a non-liquid crystalline monomer (decanediol methacrylate) and a liquid crystalline monomer (2,5-bis-[10-(oxymethacryloyl) decoxy]terephthalic acid dicholesteryl ester) was produced according to Table 1. The material properties of the securing cements were then determined. As is clear from Table 2, the conventional dental material has a polymerization shrinkage almost twice as great as the material according to the invention. The mechanical properties of the hardened cements are comparable.

TABLE 1

| Raw material | Convent. cement content (% by wt.) | "Liquid crystalline" cement content (% by wt.) |
|---|---|---|
| RM-3(urethanedimethacrylate) | 31.60 | 32.90 |
| Decanediol dimethacrylate | 7.80 | — |
| 2,5-bis-[10-(oxymethacryloyl)decoxy]terephthalic acid dicholesteryl ester | — | 8.12 |
| Aerosil OX-50 silanized | 41.42 | 39.01 |
| Ytterbium trifluoride | 18.70 | 19.47 |
| Camphor quinone | 0.24 | 0.25 |
| N,N-diethyl-3,5-di-tert.-butylaniline | 0.23 | 0.24 |
| 3,5-di-tert.-butyl-4-hydroxytoluene (BHT) | 0.01 | 0.01 |

TABLE 2

| Material property* | Convent. cement | "Liquid crystalline" cement |
|---|---|---|
| Polymerization shrinkage | 4.86% by vol. | 2.80% by vol. |
| Flexural strength according to ISO 4049 | 86 MPa | 79.5 MPa |
| Flexural modulus according to ISO 4049 | 3.19 GPa | 4.09 GPa |

*Testpiece was hardened by 2 × 3 minutes irradiation in the Spectramat

We claim:

1. A Polymerizable liquid crystalline monomer according to the formula

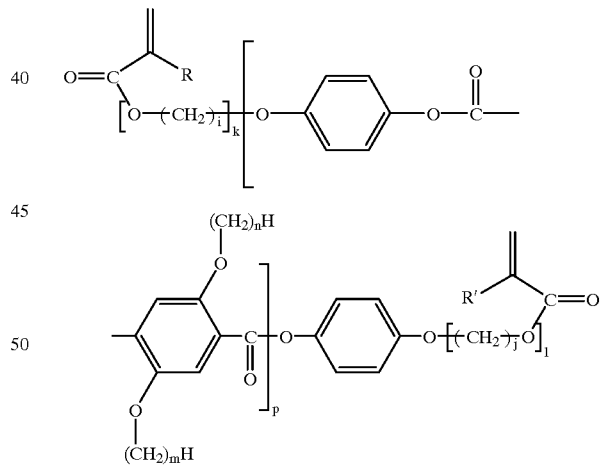

characterized in that

R, R'=H or CH$_3$ i, j=0 to 18 k, l=1 to 10 m, n=1 to 30 p=1 to 10.

2. A Polymerizable liquid crystalline monomer according to the formula

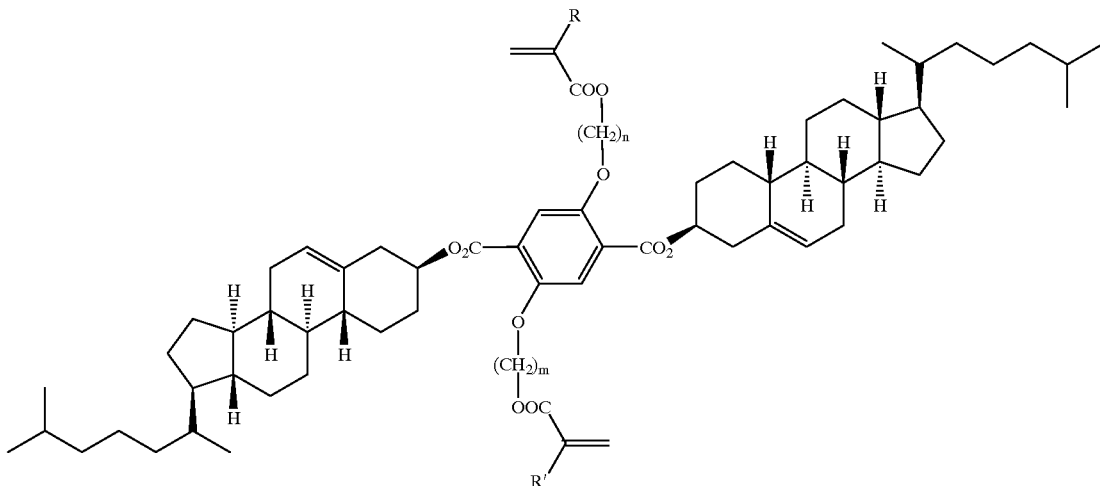

characterized in that

R, R'=H or CH$_3$ m, n=1 to 30.

3. A dental material comprising:
  at least one polymerizable monomer which has liquid crystalline properties produced by mesogenic groups;
  at least one filler; and
  a polymerization initiator which initiates polymerization of the at least one polymerizable monomer.

4. The dental material according to claim 3, wherein the at least one polymerizable monomer has liquid crystalline properties in the range from 10 to 150° C.

5. The dental material according to claim 3, characterized in that the at least one polymerizable monomer which has the liquid crystalline properties has from 1 to 6 polymerizable groups.

6. The dental material according to claim 5, characterized in that the polymerizable groups are selected from the group consisting of one or more ethylenically unsaturated groups, one or more epoxide groups, vinyl ether, 1,3-dioxolane, 1,3-dioxepane, spiro-orthoester, and spiro-orthocarbonate groups.

7. The dental material according to claim 3, characterized in that the at least one polymerizable monomer which has liquid crystalline properties contains 1, 2 or 3 mesogenic groups.

8. A dental material comprising:
  at least one polymerizable monomer which has liquid crystalline properties produced by mesogenic groups, characterized in that the mesogenic groups are selected from a group consisting of one or more aromatic carboxylic acid ester groups and one or more steriod groups and
  a polymerization initiator which initiates polymerization of the at least one polymerizable monomer.

9. The dental material according to claim 8, characterized in that the mesogenic group comprises a 2,5-alkoxy-terephthalate group.

10. A dental material according to claim 9, characterized in that it contains as liquid crystalline monomer a derivative of formula

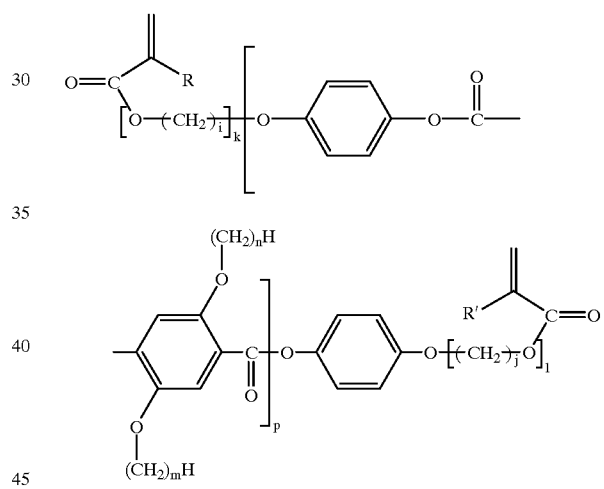

in which

R, R'=H or CH$_3$ i, j=0 to 18 k, l=1 to 10 m, n=1 to 30 p=1 to 10.

11. A dental material according to claim 9, characterized in that it contains as liquid crystalline monomer a derivative of formula

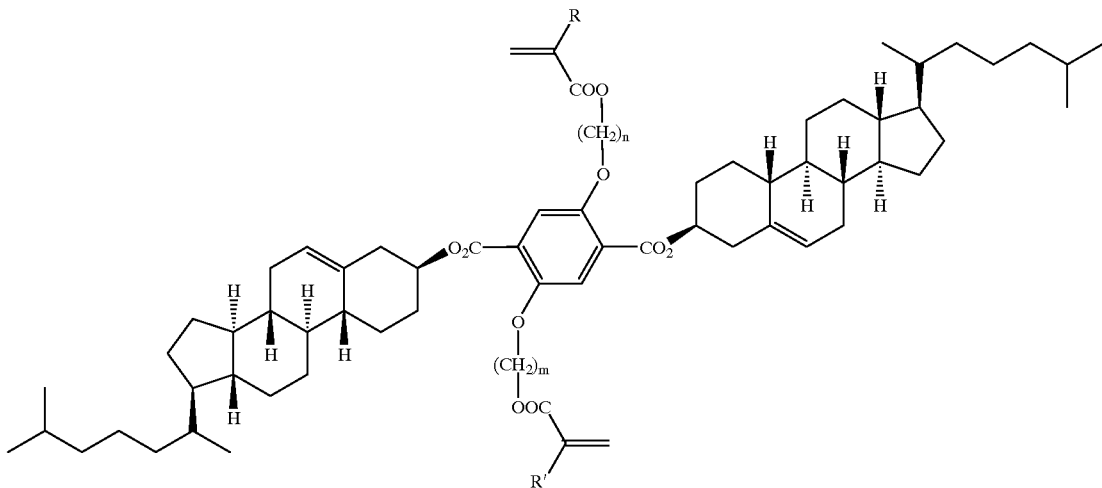

in which

R, R'=H or CH$_3$ m, n=1 to 30.

12. A dental material comprising:
at least one polymerizable monomer which has liquid crystalline properties produced by mesogenic groups at temperatures of 10 to 75° C.; and
a polymerization initiator which initiates polymerization of the at least one polymerizable monomer.

13. A method of producing a polymerized dental material comprising:

providing a polymerizable monomer with liquid crystalline properties produced by mesogenic groups at temperatures of 10 to 75° C.;

mixing the polymerizable monomer with a polymerization initiator to form a mixture; and polymerizing the mixture to produce a dental material.

14. The method of claim 13 further comprising adding a filler to the mixture prior to said polymerizing.

* * * * *